United States Patent [19]

Zehner

[11] 4,005,130
[45] Jan. 25, 1977

[54] PREPARATION OF OXALATE ESTERS FROM CARBON MONOXIDE AND ALCOHOL OVER A METAL CATALYST AND A DIONE OXIDANT

[75] Inventor: Lee R. Zehner, Media, Pa.

[73] Assignee: Atlantic Richfield Company, Los Angeles, Calif.

[22] Filed: June 26, 1975

[21] Appl. No.: 590,527

[52] U.S. Cl. .................. 260/485 R; 260/465 D; 260/465.4; 260/485 H; 260/485 J; 260/485 L; 260/485 P
[51] Int. Cl.$^2$ ............................. C07C 69/36
[58] Field of Search ........ 260/485 R, 485 H, 485 J, 260/485 L, 485 P, 465 D, 465.4

[56] References Cited

OTHER PUBLICATIONS

Fenton, J. Org. Chem. 39, (5) pp. 701–704 (1974).

*Primary Examiner*—Jane S. Myers
*Attorney, Agent, or Firm*—Delbert E. McCaslin

[57] ABSTRACT

A process for the preparation of oxalate esters by the oxidative carbonylation of alcohols with carbon monoxide in the presence of a catalytic amount of copper, nickel, cadmium, cobalt or zinc metal salt catalyst and at least a stoichiometric amount of an unsubstituted or halogen substituted 2,5-cyclohexadiene-1,4-dione. High yields and selectivity of the oxalate ester, over the carbonate ester and $CO_2$, are obtained and maximized by regulating temperature, carbon monoxide pressure and metal salt catalyst and by maintaining substantially anhydrous conditions.

10 Claims, No Drawings

PREPARATION OF OXALATE ESTERS FROM CARBON MONOXIDE AND ALCOHOL OVER A METAL CATALYST AND A DIONE OXIDANT

BACKGROUND OF THE INVENTION

A number of prior art processes have been proposed for the preparation of oxalate esters and carbonate esters by the oxidative carbonylation of alcohols with carbon monoxide. Such prior art processes encompass the use of expensive noble metal salt catalysts, oxygen, ferric or cupric salt redox systems and dehydrating agents.

The present invention is directed to an improved process for the oxidative carbonylation of alcohols wherein carbon monoxide and an alcohol are reacted at suitable temperatures and pressure conditions in the presence of specific metal salt catalysts and an unsubstituted or halogen substituted 2,5-cyclohexadiene-1,4-dione as the oxidant. The 1,4-benzene-diol or halogenated benzene diol formed as a result of the reaction can be reoxidized by known methods, e.g., with air or oxygen, to provide a cyclic process for the manufacture of the oxalate esters.

U.S. Pat. No. 3,393,136 describes a process for the preparation of oxalates by contacting carbon monoxide at superatmospheric pressure, with a saturated monohydric alcohol solution of a platinum group metal salt and a soluble ferric cupric salt (redox agent) while maintaining the salts in a highly oxidized state by the simultaneous introduction of oxygen or the application of a direct current electrical potential to the reaction zone. When oxygen is employed, explosive mixtures of oxygen and combustible organic vapors in the gas phase must be avoided and water scavengers or dehydrating agents such as alkyl orthoformic acid esters must be added to the liquid phase to prevent the accumulation of water.

A recent West German Pat. No. 2,213,435 discloses a method for the synthesis of oxalic acid and oxalate esters in water and alcohol respectively. A platinum group metal salt, a salt of a metal more electropositive than the platinum group metal, e.g. copper (II) chloride and an alkali metal salt comprise the catalyst. Oxygen in stoichiometric amounts was employed as the oxidant. A disadvantage of such reaction is that explosive mixtures of oxygen and carbon monoxide are necessary to effect reaction. Under non-explosive conditions only trace amounts of oxalate can be obtained.

In a recent article by Donald M. Fenton and Paul J. Steinwand, Journal of Organic Chemistry, Vol. 39, No. 5, 1974, pp. 701–704 the synthesis of oxalate and carbonate esters is described by reacting carbon monoxide and an alcohol in the presence of palladium (II) chloride redox systems, oxygen and dehydrating agents. The use of benzoquinone as an oxidant and palladium (II) chloride catalyst with or without a dehydrating agent is also shown. In the absence of a dehydrating agent and at low CO pressure the yields of oxalate and carbonate were 2.4 and 2.8 mole percent respectively based on the benzoquinone charged.

The oxalate products of the present invention have many important commercial applications, for example, as cellulose ether or ester resin solvents, for the preparation of pharmaceuticals and glycols and as dye intermediates.

Advantages of the present invention, as compared to prior art processes are (1) high conversions and high selectivity to oxalate esters over the attendant carbonate ester, (2) catalysis of the oxidative carbonylation reaction with less expensive and more readily available metal salt catalysts such as copper (II) chloride and zinc chloride, (3) elimination of hazardous operational conditions by avoiding explosive mixtures of oxygen and carbon monoxide and (4) avoiding the necessity of employing dehydrating agents to remove water.

SUMMARY OF THE INVENTION

According to the present invention there is provided a much improved oxidative carbonylation process for the preparation in high yield of oxalates by reacting carbon monoxide with an alcohol, which process is carried out at elevated temperatures and pressures in the presence of a copper, nickel, cadmium, cobalt or zinc metal salt catalyst and at least a stoichiometric amount of an unsubstituted or halogen substituted 2,5-cylohexadiene-1,4-dione and under relatively anhydrous conditions.

It has been found that the above-mentioned reaction can be carried out at high conversions to the oxalate ester, over the carbonate ester which may be present in only trace amounts by conducting the reaction in the presence of specific metal salt halides, oxalates acetates and trifluoroacetates and at least a stoichiometric amount of a 2,5-cyclohexadiene-1,4-dione to provide a pronounced effect on oxalate ester selectivity.

It is a primary object of this invention to provide an improved and economical process for the preparation of oxalate esters and in high yield while avoiding operational problems associated with prior art processes.

It is another object of this invention to provide a novel reaction system useful in the conversion of carbon monoxide and alcohol to oxalate esters which may be carried out in a cyclic manner.

It is a further object of this invention to provide a specific mechanism for the employment of specific metal salt catalysts and oxidant in an oxidative carbonylation process.

A further object is to provide an improved process for the preparation of commercially important diethyl oxalate in high yield.

These and other objects and advantages of this invention will become apparent from the description of the invention which follows and from the claims.

DESCRIPTION OF THE INVENTION

In accordance with this invention, an oxalate ester is produced by reacting, under relatively anhydrous liquid phase conditions, an alcohol with carbon monoxide at elevated temperatures and pressures in the presence of an unsubstituted or halogen substituted 2,5-cyclohexadiene-1,4-dione and a catalytic amount of a copper, cobalt, cadmium, nickel or zinc metal halide, oxalate, trifluoroacetate or acetate salt. The synthesis of the oxalate esters is carried out according to the following postulated equation:

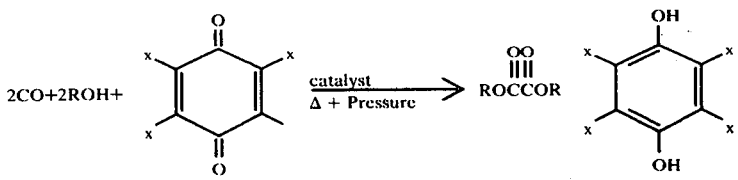

wherein R is selected from monohydric substituted or unsubstituted aliphatic, alicyclic or aromatic groups and x is hydrogen or a halogen selected from chlorine, bromine, fluorine or iodine. In the reaction the 2,5-cyclohexadiene-1,4-dione employed in at least a stoichiometric amount, functions as an oxidant and a hydrogen ion acceptor.

The reaction between the alcohol, carbon monoxide, and oxidant may be carried out in an autoclave or any other high pressure reactor. A general procedure is to charge the alcohol, catalyst, and the oxidant into the reactor vessel, introduce the proper amount of carbon monoxide to obtain the desired reaction pressure and then heat the mixture to the desired temperature for the appropriate period. The reaction can be carried out batchwise or as a continuous process and the order of addition of the reactants may be varied to suit the particular apparatus employed. The reaction products are recovered and treated by any conventional method such as distillation and/or filtration, etc. to effect separation of the oxalate from unreacted materials, catalyst, oxidant, by-products, etc.

The reaction is performed and takes place under relatively anhydrous conditions, i.e., in an essentially anhydrous alcoholic media. The alcohols suitable for use in the process of the present invention and generally employed in at least stoichiometric quantities, can be monohydric saturated aliphatic and alicyclic alcohols or aromatic alcohols and may contain other substituents such as halo, amido, alkoxy, amino, carboxy, cyano, etc. radicals in addition to the hydroxyl group. The substituents, in general, do not interfere with the reaction of the invention.

The alcohols which may be primary, secondary or tertiary alcohols conform to the general formula ROH, wherein R is an optionally substituted aliphatic or alicyclic group preferably containing from 1 to 20 carbon atoms. R may also be an aromatic group containing one or more benzenoid rings preferably not more than 3 rings which may be fused or joined by single valency bonds, directly or through bridging groups which may be, for example, oxygen or sulfur atoms or sulfoxide, sulfone or carbonyl groups or alkylene groups in which, if desired, the carbon chain may be interrupted by, for example, oxygen or sulfur atoms, sulfoxide, sulfone or carbonyl groups, for example methylene, oxymethylene, dimethylene sulfone or dimethylene ketone groups. Representative alcohols especially suitable for use in this invention are monohydric alcohols such as methyl, ethyl, n-, iso-, sec-, and tert-butyl, amyl, hexyl, octyl, lauryl, n- and sec-propyl, cetyl, benzyl, chlorobenzyl and methoxybenzyl alcohols as well as, for example, cyclohexanol, octanols, heptanols, decanols, undecanols, 2-ethyl hexanol, nonanol, myristyl alcohol, stearyl alcohol, methyl cyclohexanol, pentadecanol, oleyl and eicosonyl alcohols, and the like.

The oxidants which may be employed in at least a stoichiometric amount in the process of this invention are 2,5-cyclohexadiene-1,4-dione and halogen substituted 2,5-cyclohexadiene-1,4-diones including the mono-, di-, tri and tetra-substituted chloro, bromo, fluoro and iodo compounds. In addition to 2,5-cyclohexadiene-1,4-dione per se representative halogen substituted 2,5-cyclohexadiene-1,4-diones include, for example, 2-chloro-, 2-bromo-, 2-fluoro- and 2-iodo-2,5-cyclohexadiene-1,4-diones, 2,5-, 2,6- and 2,3-dichloro-, dibromo, difluoro-, and diiodo-2,5-cyclohexadiene-1,4-diones, 2,3,5-trichloro-, tribromo-, trifluoro-, and triiodo-2,5-cyclohexadiene-1,4-diones and the 2,3,5,6-tetrachloro-(chloranil), 2,3,5,6-tetrabromo-(bromanil), 2,3,5,6-tetrafluoro- and 2,3,5,6-tetraiodo-2,5-cyclohexadiene-1,4-diones. Mixtures of the diones may also be employed. In the reaction the 2,5-cyclohexadiene-1,4-diones, substituted and unsubstituted, are converted to the respective diol, e.g., 2,3,5,6-tetra-chloro-1,4-benzenediol which may be reoxidized to the dione for recycle and reuse in the oxidative carbonylation process of the invention.

The metal salt catalyst which may be employed in the process of this invention are the copper, nickel, cadmium, cobalt and zinc salts alone or a mixture thereof. Among the chemical forms of the metal compounds which can be used are the copper, nickel, cadmium, cobalt, and zinc halides, oxalates, trifluoroacetates and acetates preferably the metal halides such as copper chlorides, nickel chloride, cobaltous chloride, cadmium chloride and zinc chloride, and the respective iodides and bromides.

The catalysts employed may be in a homogeneous state in the reaction mixture at reaction conditions. Thus, the catalysts may be present in solution, or suspension and may also be on support materials such as alumina, silica gel, activated carbon or zeolites. The supported catalyst may be in a fixed bed while carbon monoxide/alcohol/oxidant are passed over the supported catalyst bed.

The reaction is generally carried out in the presence at catalytic proportion of the metal salt catalyst and will proceed with small amounts of the metal salt catalyst compounds herein above described. Generally the proportions of the metal salt catalyst used in the reaction will be equivalent to between about 0.001 to 5 weight percent of the alcohol employed and are preferably employed in amounts between about 0.01 to 2 percent by weight of the alcohol employed. Larger or smaller amounts may be employed at varied pressures or reaction rates. A ligand or coordination complex compound of the metal catalyst may also be employed in the process of the invention as a co-catalyst, e.g., triphenyl phosphine.

The process of the invention can be operated entirely under the liquid phase conditions of the anhydrous alcohol, oxidant and catalyst. Although not required, solvents, if desired, which are chemically inert to the components of the reaction system may be employed. Suitable solvents include, for example, organic esters such as ethyl acetate, n-propyl formate, isopropyl acetate, sec-and iso-butyl acetate, amyl acetate, cyclohexyl acetate, n-propyl benzoate, lower alkyl phthalates, etc. and the alkyl sulfones and sulfoxides such as propyl ethyl sulfoxide, diisopropyl sulfone, diisooctyl sulfoxide, etc.

As indicated above the reaction can be suitably performed by introducing the carbon monoxide at a desired pressure into contact with the alcoholic reaction medium containing the specified reactants, catalysts and oxidant and heating to the desired temperature. In general, carbon monoxide pressures of about 200 psi to about 5000 psi preferably 1500 to 2000 psi may be employed as total reaction pressure. Stoichiometric quantities of carbon monoxide are generally employed. However, an excess of carbon monoxide may be employed, for example, in continuous processes where a large excess of or high carbon monoxide requirements are generally utilized, a suitable recycle of the carbon monoxide may be employed. The reaction will proceed at temperatures of from about 80° C. to 200° C. It is generally preferred to operate the process at temperatures in the range of 100° C. to 150° C. to obtain a convenient rate of reaction. Heating and/or cooling means may be employed interior and/or exterior of the reaction to maintain the temperature within the desired range.

The reaction time is generally dependent upon the alcohol being reacted, temperature, pressure and on the amount and type of catalyst and oxidant being charged as well as the type of equipment being employed. Reaction times will vary dependent on whether the process is continuous or batch. The reaction is limited by the available oxidant, alcohol and carbon monoxide.

The following examples are provided to illustrate the invention in accordance with the principles of this invention but are not to be construed as limiting the invention in any way except as indicated by the appended claims.

In the runs which follow a 300 ml. stainless steel (Magnedrive) stirred autoclave was employed and the reaction products analyzed by gas-liquid phase chromatography (glc) for the oxalate and carbonate ester.

EXAMPLE I

A number of runs were carried out in a 300 ml. stainless steel stirred autoclave. The metal catalyst, 0.185 moles of 2,5-cyclohexadiene-1,4-dione and 70 ml. of absolute ethanol were charged to the autoclave. The autoclave and its contents were purged with nitrogen. The autoclave was pressurized to 1600 psi with carbon monoxide without stirring. Stirring was begun and the reactor heated to 125° C. which was held for 1 hour after the gas uptake stopped. Yields of diethyl carbonate (DEC) and diethyl oxalate (DEO) were based on the moles of 2,5-cyclohexadiene-1,4-dione charged. The liquid products were analyzed by glc. The results are shown in Table I.

TABLE I

| Run No. | Catalyst (m moles) | Gas Analysis (mole %) | | | $DEC^{(1)}$ (mole%) | $DEC^{(2)}$ (mole %) | DEO/DEC |
| --- | --- | --- | --- | --- | --- | --- | --- |
| | | CO | $CO_2$ | $H_2$ | | | |
| 1 | CuBr 2.82 | 97.4 | 4.5 | 0.2 | 10.8 | 41.5 | 3.8 |
| 2 | $CuCl_2$ 2.82 | 95.1 | 4.1 | 0.1 | 9.4 | 36.5 | 3.9 |
| 3 | $Cu(II)Y^{(3)}$ 4.52 g. | 95.5 | 3.5 | 0.0 | 9.4 | 24.8 | 2.6 |
| 4 | CuCl 2.82 | 98.2 | 1.0 | 0.1 | 4.7 | 16.8 | 3.6 |
| 5 | $NiBr_2$ 2.82 | 93.9 | 5.4 | 0.0 | 12.0 | 26.6 | 2.2 |
| 6 | $NiCl_2$ 2.82 | Not Measured | | | 9.3 | 22.3 | 2.4 |
| 7 | $CoCl_2$ 2.82 | 96.9 | 3.1 | 0.0 | 6.7 | 22.2 | 3.3 |
| 8 | $CdCl_2$ 2.82 | 97.1 | 2.2 | 0.0 | 4.9 | 18.6 | 3.8 |
| 9 | $ZnCl_2$ 2.82 | 98.6 | 0.7 | 0.0 | 2.8 | 8.6 | 3.1 |

EXAMPLE II

Run No. 2 of Table I, Example I was repeated except the initial pressure was reduced from 1600 to 800 psi CO. The yields of diethyl oxalate and diethyl carbonate were 19.7 and 17.4 mole percent respectively.

EXAMPLE III

A number of runs were made in a 300 ml. stainless steel autocalve using various metal salt catalysts, absolute ethanol and dione compounds as oxidants charged to the autoclave. The reactor and its contents were purged with nitrogen. The autoclave was pressured to 1600 psi with carbon monoxide without stirring. Stirring was begun and the reactor heated to 125° C. and held for 1 hour after the gas uptake ceased. Yields of diethyl oxalate (DEO) and diethyl carbonate (DEC) were calculated relative to the moles of dione charged and analyzed by gas-liquid phase chromatography. The results are shown in Table II.

TABLE II

| Run No. | Catalyst (m moles) | Dione Oxidant (moles) | Ethanol (ml) | DEC (mole %) | DEO (mole %) | DEO/DEC |
| --- | --- | --- | --- | --- | --- | --- |
| 1 | $CdBr_2$ 8.46 | CHLOR. 0.093 | 150 | 8.3 | 31.5 | 3.8 |
| 2 | $CuCl_2$ 2.82 | CHLOR. 0.093 | 150 | 16.1 | 48.8 | 3.0 |
| 3 | $CuCl_2$ 2.82 | DQ 0.122 | 70 | Trace | Trace | — |

TABLE II-continued

| Run No. | Catalyst (m moles) | Dione Oxidant (moles) | Ethanol (ml) | DEC (mole %) | DEO (mole %) | DEO/DEC |
|---|---|---|---|---|---|---|
| 4 | $CuCl_2$ 2.82 | ANQ 0.185 | 70 | 0.0 | 0.0 | — |

CHLOR.: p-chloranil.
DQ: duroquinone.
ANQ: 9,10-anthraquinone.

EXAMPLE IV

A run similar to Run No. 2 of Table II, Example III was made in which the amount of copper (II) chloride was increased to 5.64 moles, the initial CO pressure increased to 1800 psi, and the reaction temperature decreased to 90° C. No gas uptake was observed at reaction temperature. The liquid product contained only trace amounts of diethyl carbonate and diethyl oxalate.

EXAMPLE V (Comparative)

This run demonstrates that halogen substituted ortho-benzoquinone does not perform as a satisfactory oxidant.

To the stirred autoclave was charged 0.38 g. copper (II) chloride, 20.00 g. tetrachloro-ortho-benzoquinone, and 70 ml. absolute methanol. Nitrogen was purged through the reactor for 10 minutes. 1600 psi carbon monoxide was charged with stirring. The temperature was raised to 125° C. and held for 60 minutes without any pressure drop. Upon cooling to ambient temperature, analysis of the reaction product showed the absence of dimethyl oxalate and dimethyl carbonate.

EXAMPLE VI

To the autoclave was charged 0.50 g. cobalt (II) bromide, 20.00 g. 2-chloro-2,5-cyclohexadiene-1,4-dione, and 70 ml. 2-propanol. A 10 minute nitrogen purge was carried out. 2000 psi CO was charged with stirring. The temperature was raised to 130° C. and held for 150 minutes. The reactor was cooled to ambient temperature. Quantitative glc analysis of the liquid reaction product showed a yield of diisopropyl oxalate and a lesser amount of diisopropyl carbonate.

EXAMPLE VII 0.45 g. nickel (II) iodide, 22.5 g. 2,3,5,6-tetrabromo-2,5-cyclohexadiene-1,4-dione, and 70 ml. n-butanol were charged to the high pressure autoclave. A 10 minute nitrogen purge was performed. 2000 psi CO was charged to the reactor, which was subsequently heated to 110° C. The temperature was held for 120 minutes, during which time a pressure drop was noted. The reactor was cooled to ambient temperature, and the liquid product was shown to contain di-n-butyl oxalate and a lesser amount of di-n-butyl carbonate.

EXAMPLE VIII

To the stirred autoclave were added 0.27 g. copper (I) iodide, 25.00 g. 2,5-dichloro-2,5-cyclohexadiene-1,4-dione, and 70 ml absolute ethanol. The contents of the reactor were purged with nitrogen for 10 minutes. 3000 psi CO was charged to the reactor with stirring. The reaction temperature, 100° C. was maintained for 320 minutes. After a brief induction period, a slow uptake occurred. The reactor was cooled to room temperature. The liquid product contained 5.8 g. diethyl oxalate and 1.2 diethyl carbonate.

EXAMPLE IX

To the autoclave was added 0.50 g. zinc (II) acetate (anhydrous), 20.00 g. 2,5-cyclohexadiene-1,4-dione and 70 ml absolute methanol. A 10 minute nitrogen purge was performed. 2000 psi CO was charged, and the reactor was heated to 150° C. which temperature was maintained for 60 minutes. The autoclave was cooled to ambient temperature and the liquid products analyzed by glc showed a yield of dimethyl oxalate and a lesser amount of dimethyl carbonate.

EXAMPLE X

To the high pressure autoclave was charged 0.05 g. cobalt (II) oxalate, 20.0 g. 2,3,5-trichloro-2,5-cyclocyclohexadiene-1,4-dione and 70 ml of isopropyl alcohol. A 10 minute nitrogen purge was carried out. The autoclave was pressurized to 2000 psi with carbon monoxide with stirring and the reactor heated to 140° C. The temperature was maintained for 60 minutes and then cooled to ambient temperature. Glc analysis of the liquid reaction products showed a yield of diisopropyl oxalate and a lesser amount of diisopropyl carbonate.

I claim:

1. A process for the oxidative carbonylation of an alcohol having from 1 to 20 carbon atoms, which may contain other substituents which do not interfere with the reaction, to produce oxalate esters which comprises reacting under substantially anhydrous conditions, a saturated monohydric aliphatic or alicyclic alcohol or an aromatic alcohol selected from the group consisting of benzyl, chlorobenzyl and methoxy-benzyl alcohols with carbon monoxide at a pressure of from 200 psi to 5000 psi and at a temperature in the range of about 80° to 200° C. in the presence of an effective amount of a catalyst selected from the group consisting of a copper, nickel, cobalt, cadmium and zinc metal salt compounds and at least a stoichiometric amount of a 2,5-cyclohexadiene-1,4-dione oxidant having the formula

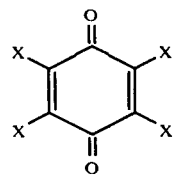

wherein x may be hydrogen or halogen and recovering the desired oxalate ester.

2. A process according to claim 1 wherein the catalyst is selected from the group consisting of copper, nickel, cobalt, cadmium and zinc halides, oxalates, trifluoroacetates and acetates.

3. A process according to claim 2 wherein the catalyst is selected from the group consisting of copper bromide, copper chloride, nickel bromide, nickel iodide, nickel chloride, cobalt chloride, cobalt bromide, cadmium chloride, cadmium bromide, and zinc chloride.

4. A process according to claim 3 wherein the catalyst is copper chloride.

5. A process according to claim 1 wherein the catalyst is a metal salt exchanged on a zeolite.

6. A process according to claim 4 wherein the catalyst is a copper salt exchanged on a zeolite.

7. A process according to claim 1 wherein the alcohol is selected from the group consisting of methyl alcohol, ethyl alcohol, isopropyl alcohol and n-butyl alcohol.

8. A process according to claim 1 wherein the oxidant is selected from the group consisting of 2,5-cyclohexadiene-1,4-dione, 2,3,5,6-tetrachloro-2,5-cyclohexadiene-1,4-dione, 2-chloro-2,5-cyclohexadiene-1,4-dione, 2,5-dichloro-2,5-cyclohexadiene-1,4-dione and 2,3,5,6-tetrabromo-2,5-cyclohexadiene-1,4-dione.

9. A process according to claim 1 wherein the pressure is between about 1500 psi and 2000 psi and the temperature is in the range of about 100° C. to 150° C.

10. A process according to claim 9 wherein the alcohol is ethanol, the catalyst is copper (II) chloride and the oxidant is 2,5-cyclohexadiene-1,4-dione or 2,3,5,6-tetrachloro-2,5-cyclohexadiene-1,4-dione.

* * * * *